(12) United States Patent
Sasaki

(10) Patent No.: US 10,575,887 B2
(45) Date of Patent: Mar. 3, 2020

(54) DISPENSING SYSTEM AND METHODS OF USE

(71) Applicant: Medtronic Holding Company Sàrl, Tolochenaz (CH)

(72) Inventor: Neil S. Sasaki, San Jose, CA (US)

(73) Assignee: Medtronic Holding Company Sàrl, Tolochenaz (CH)

( * ) Notice: Subject to any disclaimer, the term of this patent is extended or adjusted under 35 U.S.C. 154(b) by 272 days.

(21) Appl. No.: 15/668,918

(22) Filed: Aug. 4, 2017

(65) Prior Publication Data
US 2019/0038330 A1 Feb. 7, 2019

(51) Int. Cl.
*A61B 17/88* (2006.01)

(52) U.S. Cl.
CPC ...... *A61B 17/8822* (2013.01); *A61B 17/8825* (2013.01); *A61B 17/8827* (2013.01); *A61B 2017/8838* (2013.01)

(58) Field of Classification Search
CPC . A61B 17/88; A61B 17/8822; A61B 17/8825; A61B 17/8827
See application file for complete search history.

(56) References Cited

U.S. PATENT DOCUMENTS

| 4,820,275 | A | 4/1989 | Haber et al. |
| 4,850,432 | A | 7/1989 | Porter et al. |
| 5,193,907 | A | 3/1993 | Faccioli et al. |
| 5,961,211 | A | 10/1999 | Barker et al. |
| 6,302,574 | B1 | 10/2001 | Chan |
| 7,963,937 | B2 | 6/2011 | Pauser et al. |
| 8,992,541 | B2 | 3/2015 | Ferreyro et al. |
| 9,016,925 | B2 | 4/2015 | Faccioli et al. |
| 9,427,715 | B2 | 8/2016 | Palazzolo et al. |
| 2006/0256646 | A1* | 11/2006 | Bidoia ............... A61B 17/8827 366/139 |
| 2007/0185496 | A1* | 8/2007 | Beckman ........... A61B 17/8816 606/93 |
| 2008/0065088 | A1 | 3/2008 | Hughes et al. |
| 2009/0149860 | A1* | 6/2009 | Scribner ............. A61B 17/8822 606/93 |
| 2009/0171361 | A1* | 7/2009 | Melsheimer ....... A61B 17/7097 606/93 |
| 2009/0180349 | A1 | 7/2009 | Barker et al. |

FOREIGN PATENT DOCUMENTS

WO 2005123162 A1 12/2005

* cited by examiner

*Primary Examiner* — Christopher J Beccia

(57) ABSTRACT

A dispensing system includes a main body having a base and an extension extending from the base. The extension includes an inner surface defining a passageway. The main body includes an opening that extends through the extension. The opening is in communication with the passageway. A first plunger is configured to be positioned within the passageway. The first plunger includes a lumen extending through and between opposite proximal and distal end surfaces of the first plunger. A second plunger is configured to be positioned within the lumen. Kits and methods are disclosed.

20 Claims, 16 Drawing Sheets

DISPENSING SYSTEM AND METHODS OF USE

TECHNICAL FIELD

The present disclosure generally relates to medical devices, and more particularly to devices, systems and methods for dispensing a material, such as, for example, bone cement.

BACKGROUND

Many medical procedures employ medical grade bone cement in connection with the restoration and strengthening of bone structures. For example, surgeons commonly use bone cement in order to fill voids in bone. It is desirable to use bone cement, such as an adhesive bone cement, to hold small bone fragments in place to allow for healing, when methods such as traditional plate and screw methods of reattachment are not feasible. Only a small amount of bone cement may be required to fill small gaps between the bone fragments in order to glue the fragments together. For example, volumes of cement under one cubic centimeter may be used. In such applications, cement is typically dispensed to a bone to fill in voids or spaces in the bone or between medical devices or implants attached to or embedded within the bone. These dispensing devices may include systems as simple as syringes and as complex as electronically controlled valves.

The bone cement may be a mixture of different ingredients, and, before applying the bone cement to a repair site, the cement may be prepared by mixing a liquid monomer with a powder in a mixing device. The prepared bone cement can have various viscosities, and some may have quite a high viscosity, with a consistency like a tacky paste. For example, a typical adhesive bone cement may have a viscosity greater than 80 Pascal-seconds. Due to the high viscosity of the bone cement, it is often difficult to load the prepared cement into a syringe or other device. Indeed, the high viscosity of the bone cement requires a great amount of force to transfer the prepared bone cement from the mixing device to the syringe or other device. This disclosure describes improvements over these prior art technologies.

SUMMARY

In one embodiment, in accordance with the principles of the present disclosure, a dispensing system is provided that comprises a main body including a base and an extension extending from the base. The extension comprises an inner surface defining a passageway. The main body comprises an opening that extends through the extension. The opening is in communication with the passageway. A first plunger is configured to be positioned within the passageway. The first plunger comprises a lumen extending through and between opposite proximal and distal end surfaces of the first plunger. A second plunger is configured to be positioned within the lumen.

In one embodiment, in accordance with the principles of the present disclosure, a dispensing system is provided that includes a main body comprising a base and an extension extending from the base. The extension comprises an inner surface defining a passageway. The main body comprises an opening that extends through the extension. The opening is in communication with the passageway. The extension comprises a fitting. The opening extends through the fitting. The main body comprises a valve that is coupled to the fitting. The valve comprises a channel. The valve is movable between a first orientation in which the channel is offset from the opening and a second orientation in which the channel is aligned with the opening. A first plunger is movably positioned within the passageway. The first plunger comprises a lumen extending through and between opposite proximal and distal end surfaces of the first plunger. A distal end of the first plunger comprises an enlarged portion that forms a seal with the inner surface when the first plunger is inserted into the passageway. A second plunger is movably positioned within the lumen. An outer surface of the second plunger forms a seal with an inner surface of the first plunger that defines the lumen when the second plunger is inserted into the lumen. Bone cement is positioned within the lumen between the base and the plungers. A syringe is coupled to the fitting. A proximal end of the first plunger comprises a flange that engages a flange of the extension when the first plunger is fully inserted into the passageway. The flange of the first plunger engages a flange of the second plunger when the second plunger is fully inserted into the lumen.

In one embodiment, in accordance with the principles of the present disclosure, a method of dispensing a material is provided. The method comprises positioning a material in a passageway of a main body. The main body comprises a base and an extension extending from the base. The extension comprises an inner surface defining the passageway. The main body comprises an opening that extends through the extension. The opening is in communication with the passageway. A second plunger is inserted into a lumen of a first plunger. The first plunger is inserted into the passageway such that the material moves into the lumen. The second plunger is translated axially within the lumen such that the material moves through the opening.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

The present disclosure will become more readily apparent from the specific description accompanied by the following drawings, in which.

DETAILED DESCRIPTION

Figure 1:
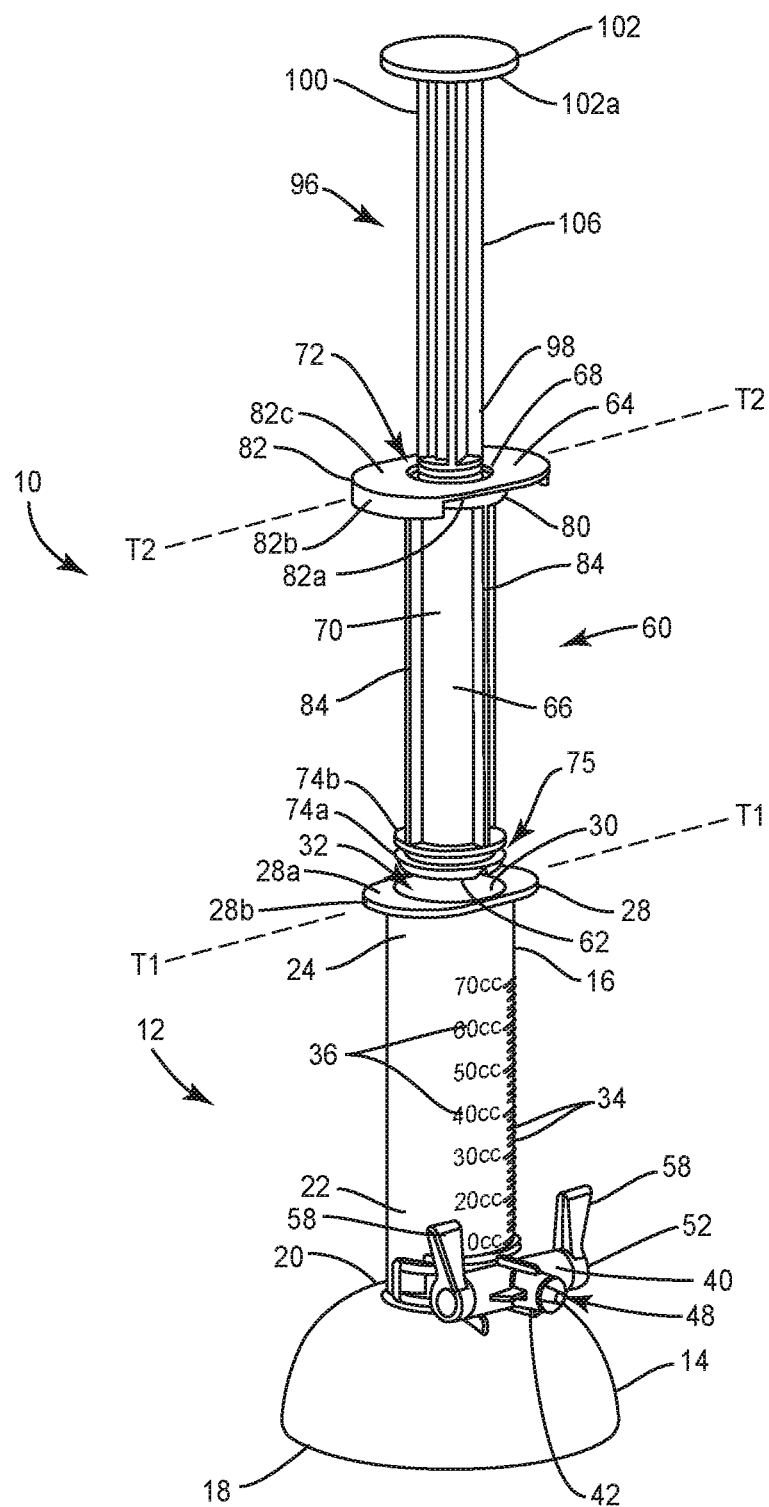
FIG. 1 is a side, perspective view of one embodiment of components of a dispensing system in accordance with the principles of the present disclosure.

The present disclosure generally relates to medical devices, and more particularly to devices, systems and methods for dispensing a material. To minimize the amount of force required to transfer and/or dispense bone cement from bone filler devices, multi-tap, or CDS cartridges, a dispensing system including a two stage plunger is provided in accordance with the principles of the present disclosure. In some embodiments, the dispensing system is similar to a telescoping hydraulic cylinder and utilizes a first stage plunger, such as, for example, an outer plunger that is hollow in the center. A second stage plunger, such as for example, an inner plunger includes a valve, such as, for example, a check valve or a vent valve. The inner plunger is inserted into the hollow portion of the outer chamber to form a plunger assembly. After bone cement is mixed within a mixer, the plunger assembly is inserted into a mixing chamber of the mixer and is advanced until the plunger assembly touches the bone cement in the mixing chamber. Air in the mixing chamber can exit the mixing chamber through the valve in the inner plunger as the plunger assembly is inserted into the mixing chamber. The outer plunger is advanced all the way down into the mixing chamber while the inner plunger is allowed to move freely. By advancing the outer plunger, the bone cement is forced into the outer plunger, which is smaller in diameter than the mixing chamber. The outer plunger is connected to the mixer by a twist lock or clips, for example, to fix the outer plunger relative to the mixer. The bone cement is then dispensed from the mixer by opening an outlet valve on the mixer and pressing the inner plunger down. Advancing the inner plunger forces the cement out through the outlet valve and into a bone filler device, multi-tap, or CDS cartridge. In some embodiments, the bone filler device is a syringe. In some embodiments, the mixing chamber has an inner diameter that is larger than the inner diameter of the outer plunger. This benefits the user as the smaller surface area of the inner plunger concentrates the force applied by the user, thus increasing the pressure they are able to generate. A change from a larger diameter to a smaller diameter increases the pressure generated with the same input force. For example, a change from a diameter of about 1.25 inches to about 0.75 inches increases the pressure generated by about 2.5 times. As such, the user can apply less force to dispense the same amount of bone cement from the mixer.

The dispensing system disclosed herein is configured to provide a plurality of benefits including, among other things, reducing the amount of force needed to dispense a material, such as, for example, bone cement. In some embodiments, the dispensing system is configured to reduce the amount of force needed to dispense the material by 2.5 times or more with the same input force. In some embodiments, the dispensing system is configured to reduce the amount of force needed to dispense the material by less than 2.5 times with the same input force. The dispensing system disclosed herein is configured to be used with known products used to mix and/or dispense materials, such as, for example syringes and other devices so as to have minimal impact on existing product validations. The dispensing system disclosed herein is configured to be low in cost. In some embodiments, one or more of the components of the dispensing system disclosed herein may be disposable. The dispensing system disclosed herein is configured to be used as a single or dual stage plunger.

In some embodiments, the dispensing system disclosed herein includes a mixer, a first stage plunger and a second stage plunger. The dispensing system disclosed herein may be used to mix and/or dispense a material, such as, for example, bone cement. In some embodiments, the bone cement may be mixed within the mixer using mixing paddles. The mixing paddles are removed after the bone cement is mixed and the two stage plunger is inserted into a mixing chamber of the mixer as an assembly. Air in the mixing chamber can escape through a vent in one of the plungers. In some embodiments, the assembly is inserted only part way into the mixing chamber. The first stage plunger is moved relative to the mixer and the second stage plunger until the first stage plunger is fully seated within the mixing chamber. By plunging the first stage plunger into the mixer, the mixed bone cement is forced into an inner cavity of the first stage plunger. The first stage plunger is connected to the mixer by a twist lock or clips, for example, such that the first stage plunger is fixed to the mixer to prevent the first stage plunger from moving axially relative to the mixer. The inner cavity of the first stage plunger has a smaller inner diameter than the mixing chamber to allow the same input force to create more pressure on the bone cement. This amplification in pressure means that less effort is needed for dispensing the bone cement from the mixer. A valve of the mixer is opened by moving one or more extensions of the valve into a delivery position. The second stage plunger is then plunged as needed until the bone cement exits the mixer and fills a cartridge, such as, for example a CDS cartridge or another device, such as, for example, a bone filler device.

As shown below, reducing the diameter of mixing chamber by allowing the bone cement to enter the inner cavity of the first stage plunger and then expelling the bone cement from the first stage plunger using the second stage plunger reduces the amount of force needed to dispense the bone cement from the mixer.

| Diameter (in) | Surface Area (in$^2$) | Lbf (est.) | Pressure (psi) | Volume (cc) | Length (in) | % increase from current |
|---|---|---|---|---|---|---|
| 1.23 (current) | 1.19 | 25 | 21.0 | 20 | 1.03 | N/A |
| 1 | 0.79 | 25 | 31.8 | 20 | 1.55 | 151% |
| 0.75 | 0.44 | 25 | 56.6 | 20 | 2.76 | 269% |
| 0.625 | 0.31 | 25 | 81.5 | 20 | 3.98 | 387% |
| 0.5 | 0.20 | 25 | 127.3 | 20 | 6.22 | 605% |
| 0.375 | 0.11 | 25 | 226.4 | 20 | 11.05 | 1076% |

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding the numerical ranges and parameters set forth herein, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

The headings below are not meant to limit the disclosure in any way; embodiments under any one heading may be used in conjunction with embodiments under any other heading.

It is noted that, as used in this specification and the appended claims, the singular forms "a," "an," and "the," include plural referents unless expressly and unequivocally limited to one referent. Thus, for example, reference to "a chemical denervation agent" or a "device" includes one, two, three or more chemical denervation agents or one, two, three or more devices.

This disclosure is directed to a dispensing system 10. In some embodiments, the components of dispensing system 10 can be fabricated from biologically acceptable materials suitable for medical applications, including metals, synthetic polymers, ceramics and bone material and/or their composites, depending on the particular application and/or preference of a medical practitioner. For example, the components of dispensing system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of dispensing system 10 may have material composites, including the above materials, to achieve various desired characteristics such as strength, rigidity, elasticity, compliance, biomechanical performance, durability and radiolucency or imaging preference. The components of dispensing system 10, individually or collectively, may also be fabricated from a heterogeneous material such as a combination of two or more of the above-described materials. The components of dispensing system 10 may be monolithically formed, integrally connected or comprise fastening elements and/or instruments, as described herein.

Dispensing system 10 includes a mixer, such as, for example, a main body 12 comprising a base 14 and an extension 16 extending from base 14. Base 14 is dome-shaped and includes opposite end surfaces 18, 20. Extension 16 extends from an end 22 that is coupled to end surface 20 and an opposite end 24. In some embodiments, end 22 is monolithically and/or integrally formed with end surface 20 such that extension 16 cannot be removed from base 14 without breaking base 14 and/or extension 16. In some embodiments, extension 16 is removably coupled to base 14. In some embodiments, extension 16 can be variously connected with base 14, such as, for example, frictional engagement, threaded engagement, mutual grooves, screws, adhesive, nails, barbs and/or raised element.

In some embodiments, end surfaces 18, 20 are each planar and extend parallel to one another. In some embodiments, end surface 20 may be disposed at alternate orientations, relative to end surface 18, such as, for example, transverse, and/or other angular orientations such as acute or obtuse, co-axial and/or may be offset or staggered. An outer surface of base 14 is convexly curved from end surface 18 to end surface 20. In some embodiments, the outer surface of base 14 is continuously curved from end surface 18 to end surface 20. In some embodiments, the outer surface of base 14 has a continuously radius of curvature from end surface 18 to end surface 20. Base 14 has a maximum height that is defined by the distance from end surface 18 to end surface 20. In some embodiments, base 14 is hollow to reduce the material used to form base 14. In some embodiments, base 14 is substantially hollow and includes one or a plurality of support structures, such as, for example, ribs 26, as shown in FIGS. 2, 3, 5, 6 and 11, to provide strength and/or rigidity to base 14. In some embodiments, base 14 includes a plurality of ribs 26 that define a grid pattern, with each of ribs 26 having opposite ends that each engage an inner surface of base 14.

Figure 9:
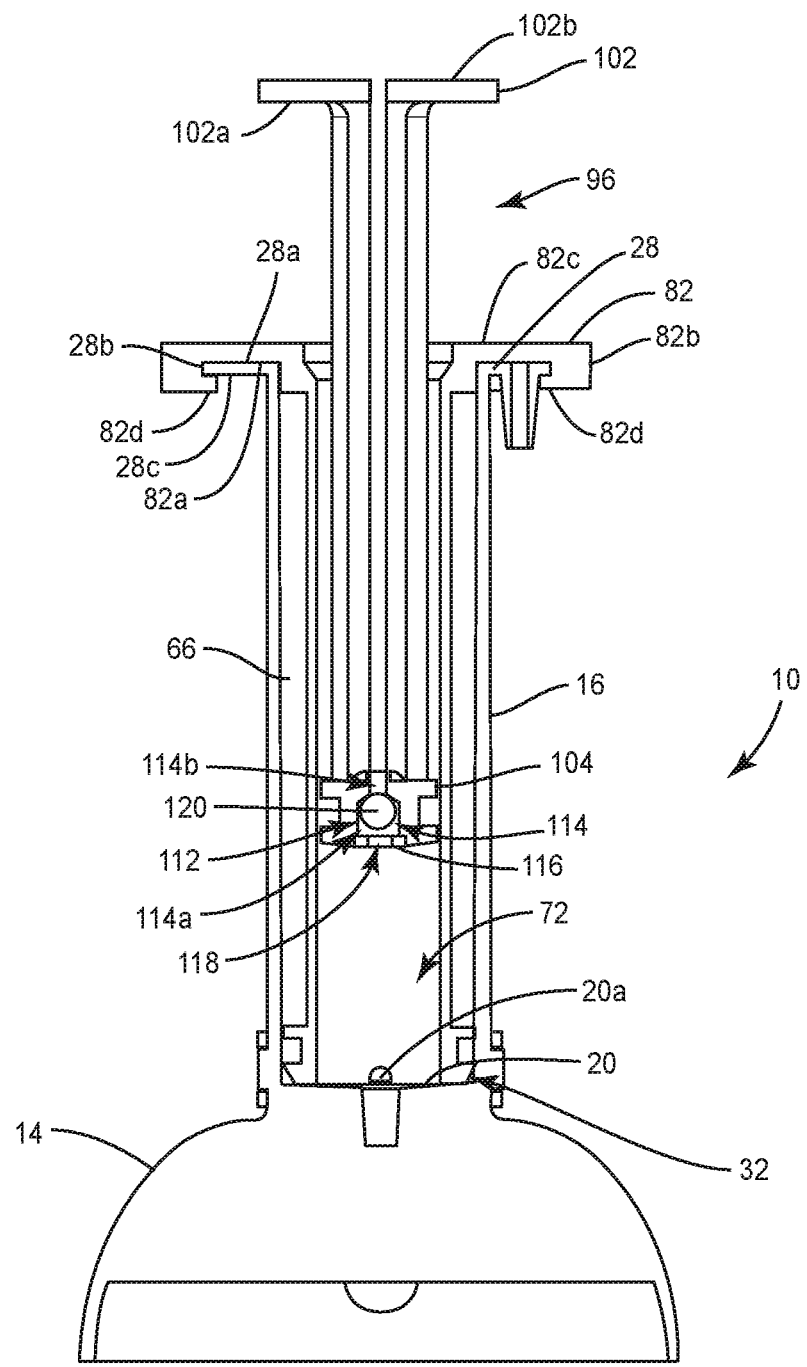
FIG. 9 is a side, cross sectional view of components of the system shown in FIG. 1.

Extension 16 is substantially cylindrical. End 24 of extension 16 includes a flange 28 that extends outwardly from an outer surface of extension 16 such that flange 28 defines a maximum width of extension 16. In some embodiments, flange 28 has an oblong cross sectional configuration such that flange 28 has a maximum diameter along a transverse axis T1, as shown in FIG. 1. Extension 16 comprises an inner surface 30 that defines a mixer chamber, such as, for example, a passageway 32 that extends through flange 28. End surface 20 of base 14 defines a distal limit of passageway 32, as shown in FIG. 9, for example. Passageway extends through flange 28. Passageway 32 has a uniform diameter along the entire length of passageway 32. Passageway 32 has a circular cross sectional configuration. In some embodiments, flange 28 and/or passageway 32 may have various cross section configurations, such as, for example, circular, oval, oblong, triangular, rectangular, square, polygonal, irregular, uniform, non-uniform, variable, tubular and/or tapered. In some embodiments, the outer surface of extension 16 includes markings, such as, for example, graduated lines 34 and indicia 36 that indicate the volume of a material M positioned within passageway 32.

Figure 4:
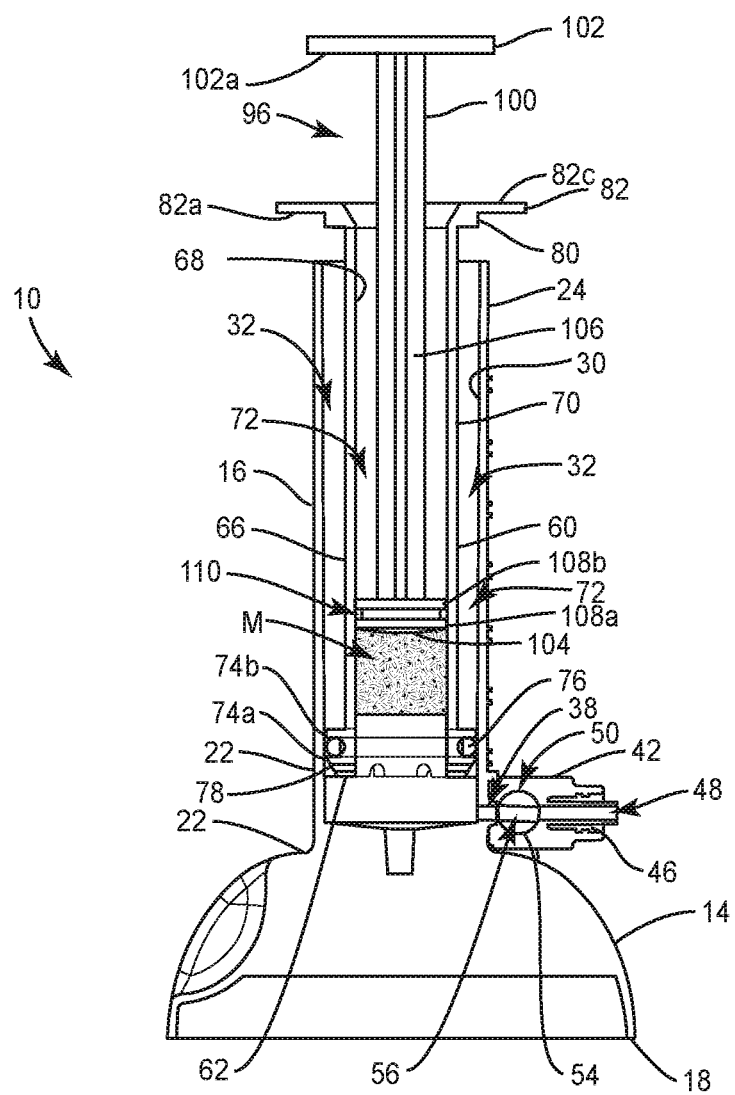
FIG. 4 is a side, cross sectional view of components of the system shown in FIG. 1.

Extension 16 comprises a single opening 38 that extends through and between surface 30 and the outer surface of extension 16, as best shown in FIG. 4. Opening 38 is in communication with passageway 32 and extends perpendicular to surface 30 and the outer surface of extension 16. In some embodiments, opening 38 may be disposed at alternate orientations, relative to surface 30 and the outer surface of extension 16, such as, for example, transverse and/or other angular orientations such as acute or obtuse, co-axial and/or may be offset or staggered.

Main body 12 includes a fitting 40 that is coupled to extension 16. Fitting 40 includes a hub 42 that is configured to couple main body 12 to another component of dispensing system 10, such as, for example, a syringe 44 (FIG. 6), via a threaded configuration or a Luer lock, as discussed herein. For example, in one embodiment, hub 42 may include an internal thread 46 (FIG. 4) that mates with an external thread on one end of syringe 44 to couple syringe 44 to hub 42. Hub 42 includes a duct 48 and a cavity 50 that extends perpendicular to duct 48, as best shown in FIG. 4. Fitting 40 includes a valve 52 having a valve body 54 that is rotatably positioned in cavity 50. In some embodiments, cavity 50 has a circular cross sectional configuration and valve body 54 is cylindrical to facilitate rotation of valve body 54 within cavity 50. A channel 56 extends through the width of valve body 54, as best shown in FIG. 4. In some embodiments, valve 52 includes ears or tabs 58 at opposite ends of valve body 54 body to facilitate rotation of valve body 54 within cavity 50 to move valve 52 between a first orientation, shown in FIGS. 1-3, 7, 8 and 12, in which valve body 54 blocks channel 56 and a second orientation, shown in FIGS. 4-6, in which channel 56 is aligned with opening 38 and duct 48, as discussed herein. That is, channel 56 is not aligned with opening 38 or duct 48 when valve 52 is in the first orientation.

An outer or first stage plunger, such as, for example, plunger 60 is configured for movable disposal in passageway 32. Plunger 60 extends from an end surface 62 to an opposite end surface 64. Plunger 60 includes a wall 66 comprising opposite inner and outer surfaces 68, 70. Surface 68 defines a lumen 72 that extends between and through end surfaces 62, 64. Lumen 72 has a uniform diameter along the entire length of lumen 72. Lumen 72 has a circular cross sectional configuration. In some embodiments, lumen 72 may have various cross section configurations, such as, for example, oval, oblong, triangular, rectangular, square, polygonal, irregular, uniform, non-uniform, variable, tubular and/or tapered. Mien material M is positioned within passageway 32, material M may enter lumen 72 when plunger 60 is positioned within passageway 32, as discussed herein.

Figure 12:
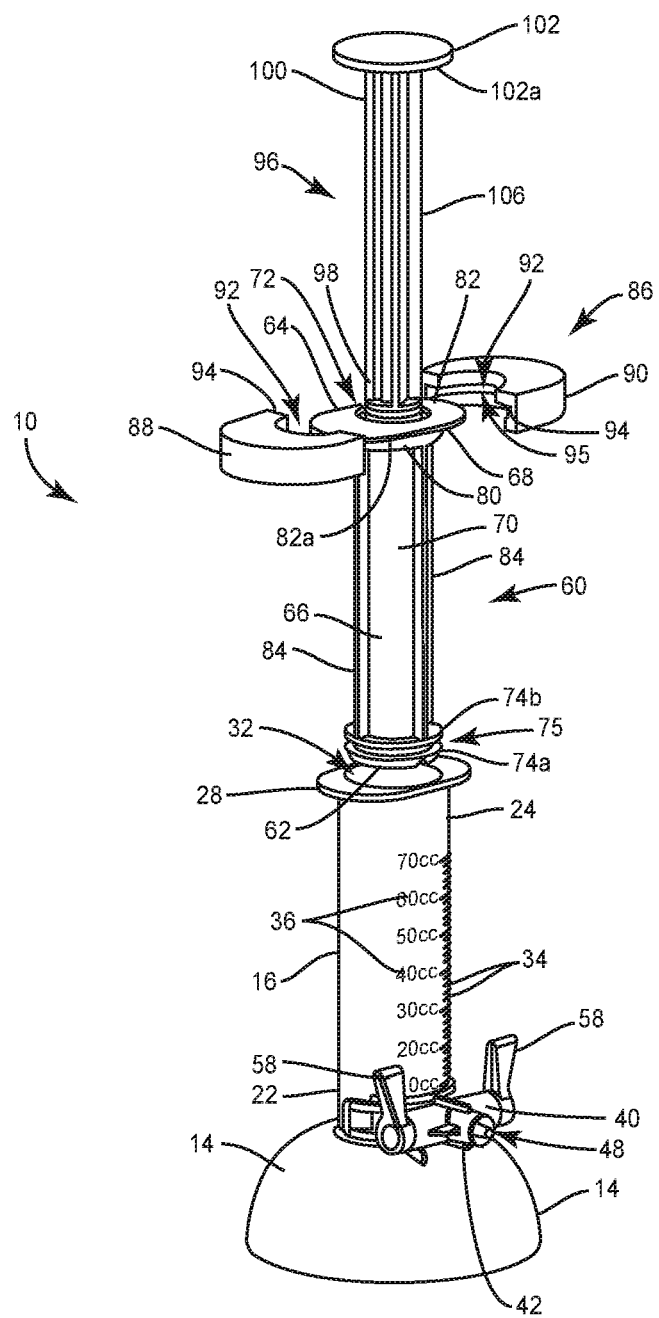
FIG. 12 is a side, perspective view of one embodiment of components of the system shown in FIG. 1.

A distal end of plunger 60 includes an enlarged portion comprising a pair of spaced apart circumferential lips 74a, 74b that each extend outwardly from surface 70. Lips 74a, 74b define a groove 75 therebetween, as shown in FIGS. 1 and 12, for example. In some embodiments, a gasket, such as, for example, an O-ring 76 is positioned in groove 75 such that outer surfaces of lips 74a, 74b and/or O-ring 76 form an air tight and/or water tight seal with surface 30 when plunger 60 is positioned within passageway 32 of extension 16. Lips 74a, 74b and/or O-ring 76 maintain the seal as plunger 60 moves axially in opposite directions within passageway 32. In some embodiments, wall 66 and/or lips 74a, 74b may be formed from a rigid material, such as, for example, one or more of the materials discussed herein. Lips 74a, 74b may be integrally and/or monolithically formed with wall 66. In some embodiments, O-ring 76 may be formed of a material that is different than the material that forms wall 66 and/or lips 74a, 74b. In some embodiments, O-ring 76 may be formed from an elastomeric material. In some embodiments, O-ring 76 is removable. Plunger 60 is shown in FIGS. 1 and 12 with O-ring 76 removed. In some embodiments, plunger 60 comprises a tapered portion 78 that extends distally from lip 74a, as shown in FIG. 4. A lower surface of portion 78 defines end surface 62. In some embodiments, portion 78 is formed from the same material that forms wall 66 and/or lips 74a, 74b. In some embodiments, portion 78 is formed from material that is different than the material that forms wall 66 and/or lips 74a, 74b. In some embodiments, portion 78 is formed from an elastomeric material such that end surface 62 forms a seal with end surface 20 when end surface 62 contacts end surface 20.

In some embodiments, proximal end of plunger 60 includes an enlarged portion comprising a circumferential lip 80 that extends outwardly from surface 70. In some embodiments, wall 66 and/or lip 80 may be formed from a rigid material, such as, for example, one or more of the materials discussed herein. Lip 80 may be integrally and/or monolithically formed with wall 66. The proximal end of plunger 60 includes a flange 82 positioned proximally of lip 80. In some embodiments, flange 82 has an oblong cross sectional configuration such that flange 82 has a maximum diameter along a transverse axis T2, as shown in FIG. 1. An upper surface of flange 82 defines end surface 64. Flange 82 has a maximum diameter that is greater than maximum diameter of lip 80 and passageway 32 such that flange 82 is prevented from entering passageway 32. A bottom surface 82a of flange 82 is configured to directly engage a top surface 28a of flange 28 when plunger 60 is fully inserted into passageway 32. In some embodiments, flange 82 includes a sidewall 82b that overlaps a sidewall 28b of flange 28 when surface 82a of flange 82 directly engages surface 28a of flange 28, as discussed herein. Plunger 60 is configured such that lip 80 is positioned within passageway 32 when surface 82a of flange 82 directly engages surface 28a of flange 28 and sidewall 82b of flange 82 overlaps a sidewall 28b of flange 28. Plunger 60 is configured such that end surface 62 of plunger 60 directly engages end surface 20 when surface 82a of flange 82 directly engages surface 28a of flange 28. In some embodiments, flange 82 may have various cross section configurations, such as, for example, circular, oval, circular, triangular, rectangular, square, polygonal, irregular, uniform, non-uniform, variable, tubular and/or tapered.

In some embodiments, plunger 60 includes spaced apart struts 84 that each extend continuously from lip 74b to lip 80. Struts 84 are disposed radially about wall 66. In some embodiments, struts 84 are evenly spaced apart from one another. Struts 84 each have a convexly curved outer surface such that the outer surfaces of struts 84 are flush with the outer surfaces of lips 74b, 80. The outer surfaces of struts 84 are continuously curved along the length of struts 84 and conform to the curvature of surface 30 of extension 16 such that the outer surfaces of struts 84 directly engage surface 30 and form an air tight and/or water tight seal with surface 30 as plunger 60 translates axially in opposite directions within passageway 32. When the outer surfaces of struts 84 directly engage surface 30, surface 70 of wall 66 is spaced apart from surface 30, as shown in FIGS. 2-6.

Figure 7:
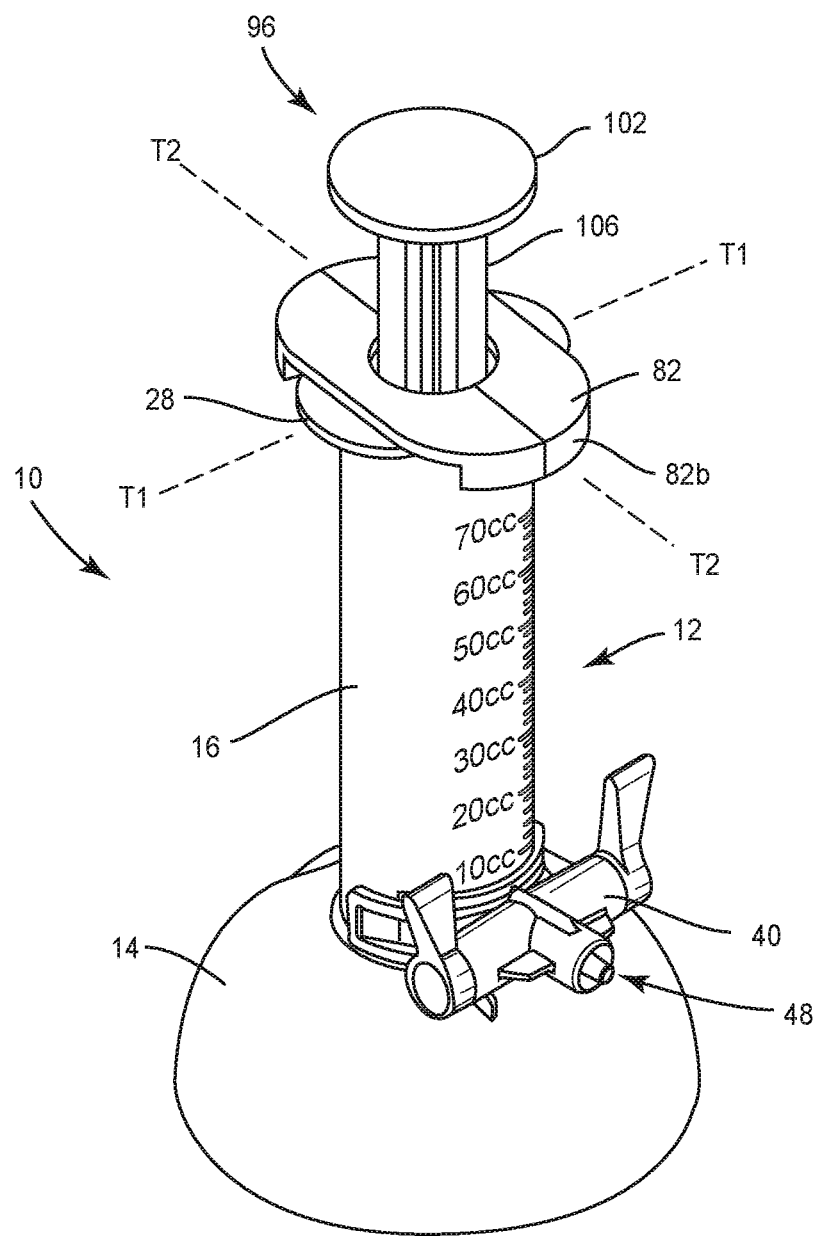
FIG. 7 is a side, perspective view of components of the system shown in FIG. 1.
Figure 8:
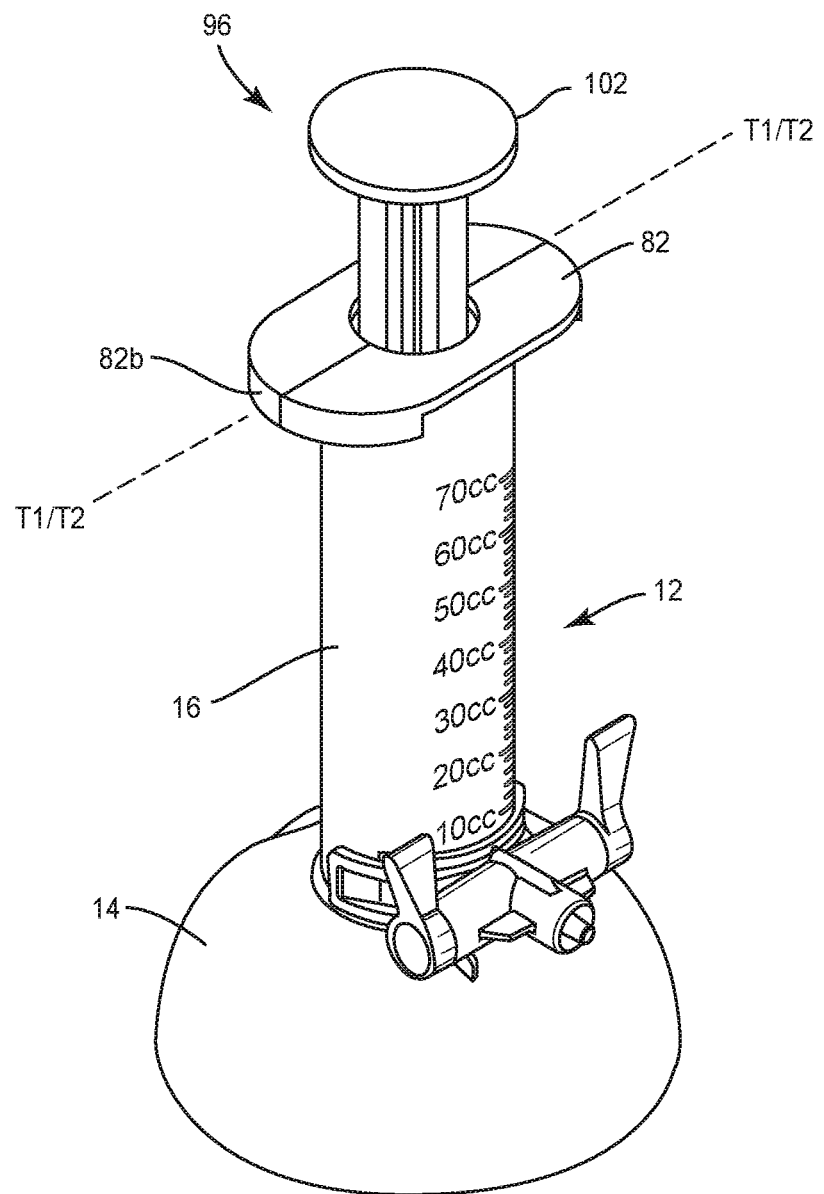
FIG. 8 is a side, perspective view of components of the system shown in FIG. 1.
Figure 10:
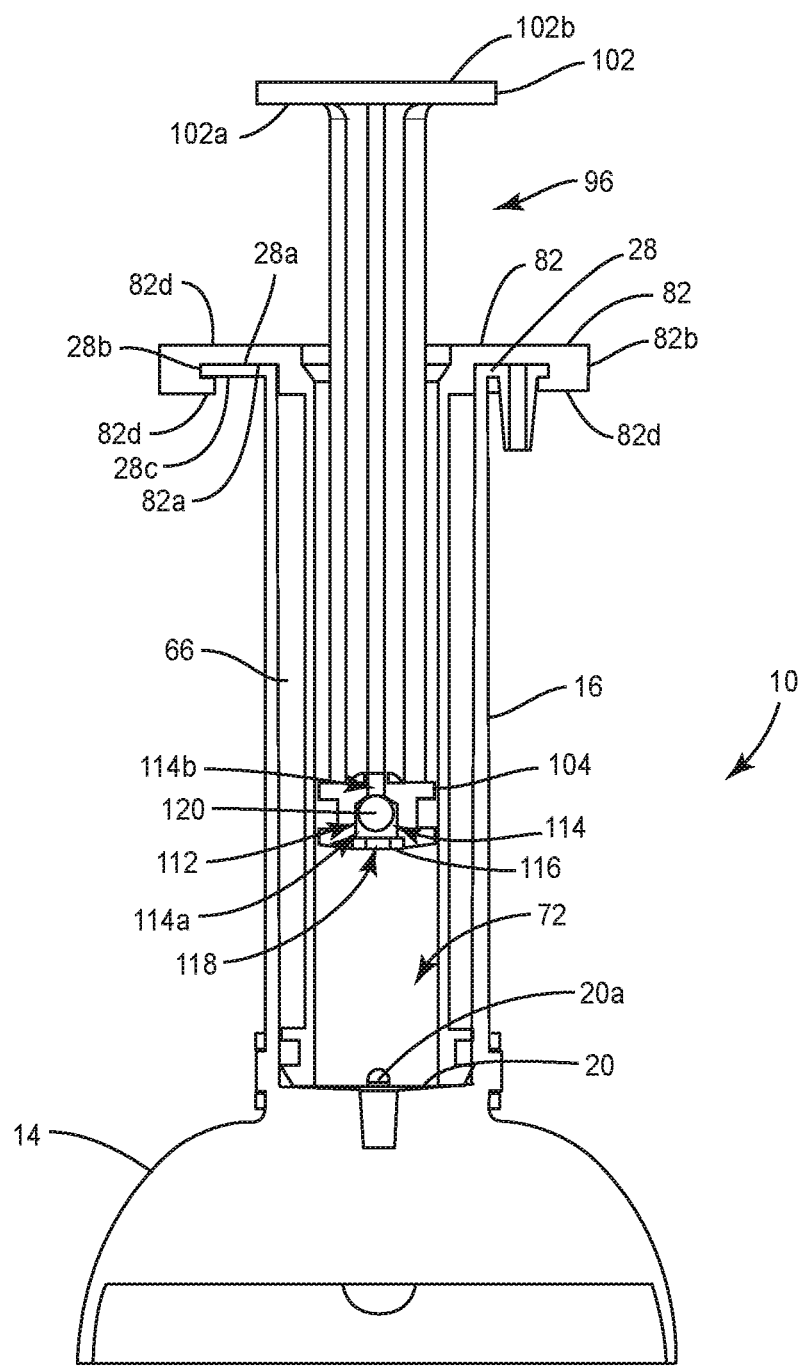
FIG. 10 is a side, cross sectional view of components of the system shown in FIG. 1.
Figure 11:
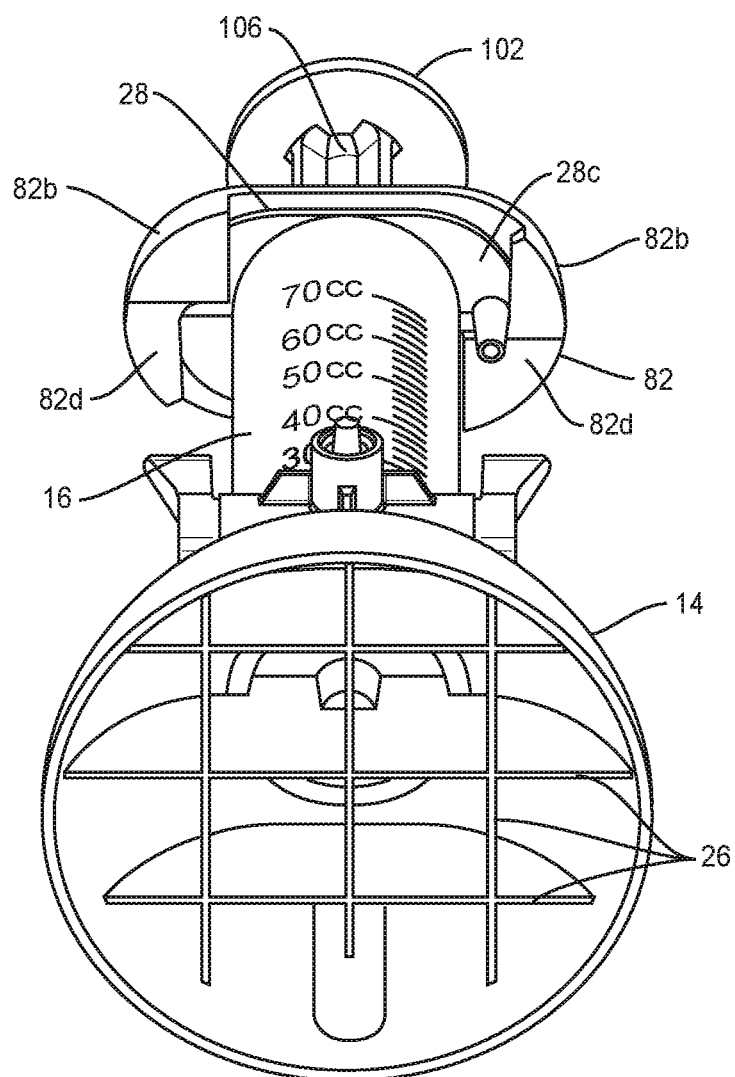
FIG. 11 is a bottom, perspective view of components of the system shown in FIG. 1.

In some embodiments, flange 82 of plunger 60 forms a twist lock with flange 28 of extension 16, as shown in FIGS. 7-11, to connect plunger 60 with extension 16 such that plunger 60 is prevented from moving axially in opposite directions relative to extension 16 within passageway 32. Flange 82 of plunger 60 includes an inward projection 82d having a vertical surface that faces wall 66 of plunger 60, as shown in FIGS. 9-11. A top surface of projection 82d faces bottom surface 82a of flange 82 and is configured to directly engage a bottom surface 28c of flange 28 when the twist lock is in a locked position, as shown in FIGS. 9-11. In particular, plunger 60 is inserted into passageway 32 and is moved axially relative to extension 16 in the direction shown by arrow A in FIG. 2 until plunger 60 is fully inserted into passageway 32 and axis T1 extends transverse to axis T2, as shown in FIG. 7. In some embodiments, axis T1 may extend perpendicular to axis T2. When axis T1 extends transverse to axis T2, the twist lock is in an unlocked position such that plunger 60 is free to translate axially relative to extension 16. Plunger 60 is then rotated in a clockwise direction or counterclockwise direction relative to extension 16 such that axis T1 is parallel and/or coaxial with axis T2, as shown in FIG. 8. In some embodiments, plunger 60 is rotated 90 degrees in a clockwise direction relative to extension 16 until axis T1 is parallel and/or coaxial with axis T2. When axis T1 is parallel and/or coaxial with axis T2 the twist lock is in the locked position, which prevents plunger 60 from moving axially in opposite directions relative to extension 16 within passageway 32. It is envisioned that plunger 60 may be locked with extension 16 using other locking mechanisms to prevent plunger 60 from translating axially in opposite directions relative to extension 16. For example, in some embodiments, lip 80 may include an outer thread that mates with an inner thread of inner surface 30 of extension 16 to connect plunger 60 with extension 16 such that plunger 60 is prevented from moving axially relative extension 16 within passageway 32.

In some embodiments, system 10 includes clips, such as, for example, a cap 86 (FIG. 12) configured for disposal of flanges 28, 82 to fix plunger 60 relative to main body 12 when plunger 60 is fully inserted into passageway 32 to prevent plunger 60 from moving axially relative to extension 16 and to prevent plunger 60 from rotating relative to extension 16. That is, plunger 60 is prevented from moving axially in opposite directions when flanges 28, 82 are disposed in cap 86. Cap 86 includes a first part 88 and a second part 90. Part 90 is identical to part 88. Parts 88, 90 each include an arcuate cutout 92 that extends through opposite top and bottom surfaces of parts 88, 90. Cutouts 92 form an opening that is coaxial with lumen 72 when a lateral surface 94 of part 88 engages a lateral surface 94 of part 90. The opening defined by cutouts 92 has the same width and diameter as lumen 72 such that an inner or second stage plunger, such as, for example, a plunger 96 can be inserted through the opening defined by cutouts 92 and into lumen 72, as discussed herein. Parts 88, 90 each include a lateral cavity 95 positioned between the top and bottom surfaces of parts 88, 90. Cavities 95 are each configured for disposal of portions of flanges 28, 82 when surface 94 of part 88 engages surface 94 of part 90.

Plunger 96 extends between an end 98 and an end 100. End 100 includes a flange 102 having a diameter that is greater than the diameter of lumen 72 such that flange 102 is not inserted into lumen 72 when plunger 96 is fully inserted into lumen 72. Rather, flange 102 engages flange 82 when plunger 96 is fully inserted into lumen 72. That is, a bottom surface 102a of flange 102 directly engages a top surface 82c of flange 82 when plunger 96 is fully inserted into lumen 72 to prevent plunger 96 from translating distally relative to plunger 60. Plunger 96 has a maximum length such that when plunger 96 is fully inserted into lumen 72, an end surface of end 98 of plunger 96 does not extend through end surface 62 of plunger 60. That is, the end surface of end 98 is positioned within lumen 72 when plunger 96 is fully inserted into lumen 72. Plunger 96 includes an enlarged tip 104 and a body 106 that extends continuously from flange 102 to tip 104. Body is cylindrical and has a uniform diameter from flange 102 to tip 104. Tip 104 has a maximum diameter that is greater than a maximum diameter of body 106. The maximum diameter of tip 104 is slightly less than the diameter of lumen 72 such that an outer surface of tip 104 directly engages surface 68 of plunger 60 to form an air tight or water tight seal with surface 68 as tip 104 moves axially within lumen 72. When the outer surface of tip 104 directly engage surface 68, the outer surface of body 106 is spaced apart from surface 68, as shown in FIGS. 2-6.

In some embodiments, body 106 and/or flange 102 may be formed from a rigid material, such as, for example, one or more of the materials discussed herein. In some embodiments, tip 104 is formed from the same material that forms body 106 and/or flange 102. In some embodiments, tip 104 is formed from material that is different than the material that forms body 106 and/or flange 102. In some embodiments, tip 104 is formed from an elastomeric material such that tip forms a seal with surface 68 when the outer surface of tip 104 contacts surface 68. In some embodiments, tip 104 includes spaced apart circumferential ridges 108a, 108b that define a groove 110 therebetween, as shown in FIG. 4. In some embodiments, a gasket, such as, for example, an O-ring similar to O-ring 76 is positioned in groove 110 such that outer surfaces of ridges 108a, 108b and/or the O-ring in groove 110 form an air tight and/or water tight seal with surface 68 when plunger 96 is positioned within lumen 72.

Figure 13:
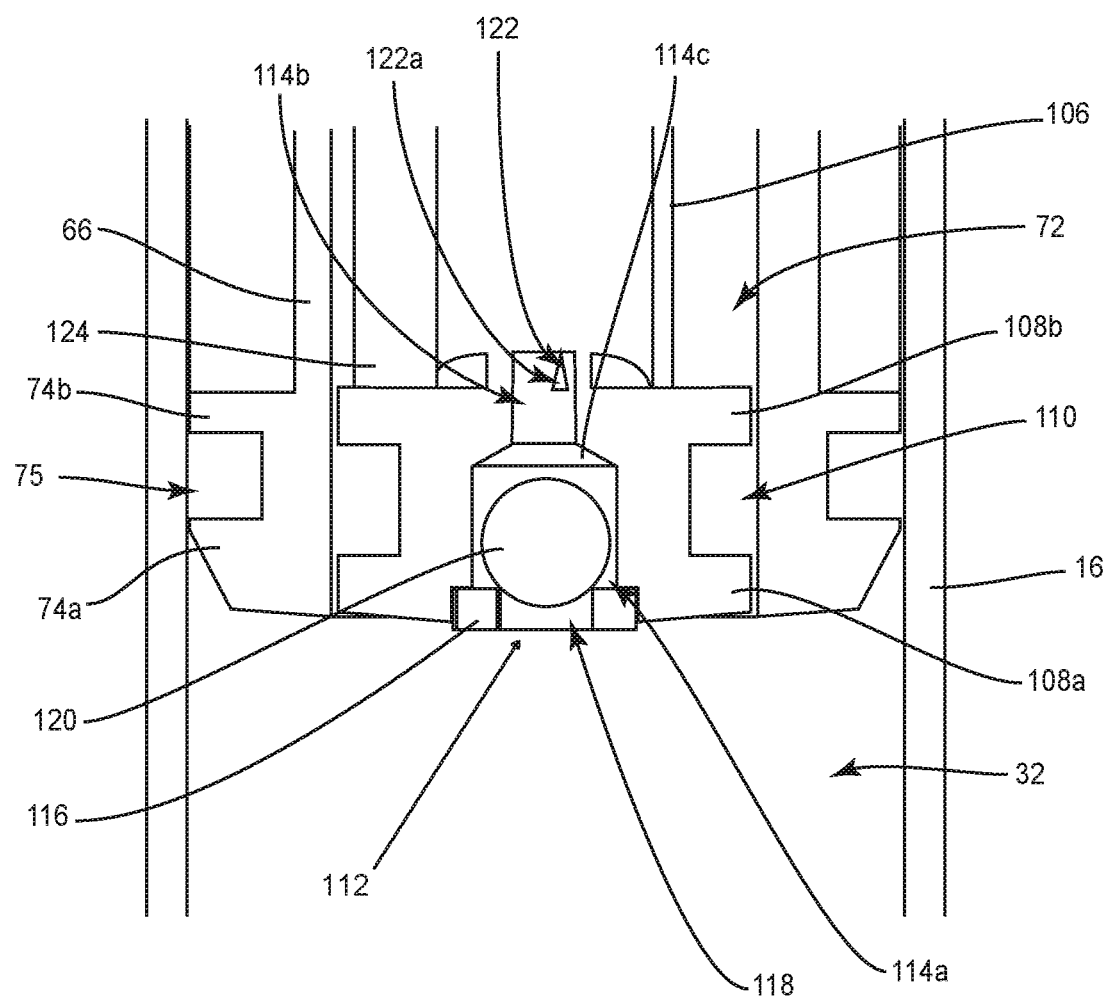
FIG. 13 is a side, cross sectional view of portions of components of the system shown in FIG. 1.
Figure 14:
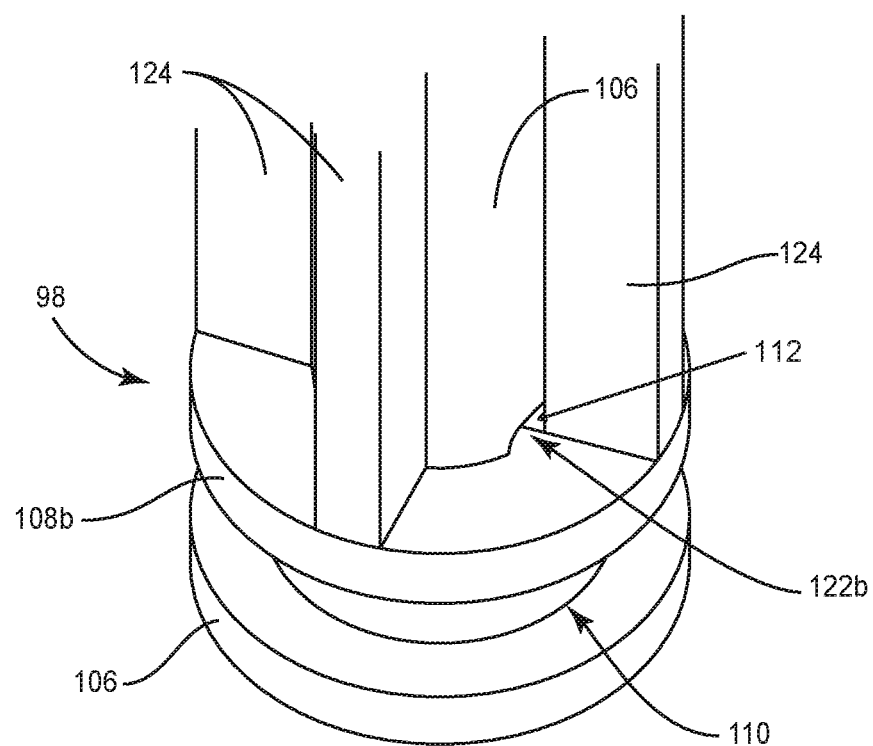
FIG. 14 is a side, perspective view of a portion of a component of the system shown in FIG. 1.

In some embodiments, plunger 96 includes a valve, such as, for example, a vent valve or a check valve 112 (FIGS. 9, 10 and 13-16) to allow air within passageway 32 and/or lumen 72 to exit plunger 96 when plunger 60 and/or plunger 96 are inserted into passageway 32, as discussed herein. Valve 112 includes a cavity 114 and a washer 116 that is positioned at the bottom of cavity 114. Washer 116 includes an opening 118 that extends through the thickness of washer 116 such that opening 118 is in communication with cavity 114. In some embodiments, opening 118 may have various cross section configurations, such as, for example, circular, oval, oblong, triangular, rectangular, square, polygonal, irregular, uniform, non-uniform, variable, tubular and/or tapered. In some embodiments, washer 116 is assembled onto tip 104 using ultrasonic welding or adhesive, for example. In some embodiments, washer 116 monolithically and/or integrally formed with tip 104. Cavity 114 includes a first portion 114a and a second portion 114b positioned above portion 114a. Portion 114a has a maximum diameter that is greater than a maximum diameter of portion 114b. In some embodiments, cavity 114 includes a tapered portion between portion 114a and portion 114b. In some embodiments, cavity 114 extends through a top surface 102b of flange 102, as shown in FIG. 9. In some embodiments, cavity 114 terminates before flange 102, such that cavity 114 does not extend through top surface 102b of flange 102, as shown in FIG. 10. Valve 112 includes a ball, such as, for example a check ball 120 movably positioned within portion 114a of cavity 114. In embodiments wherein cavity 114 does not extend through top surface 102b of flange 102, valve 112 includes a vent hole 122 having a first end 122a that is in communication with portion 114b of cavity 114, as shown in FIG. 13 and a second end 122b that extends through an outer surface of body 106 to allow air in lumen 72 and/or passageway to enter cavity 114 and exit plunger 96 through vent hole 122, as discussed herein. Ball 120 has a maximum diameter that is greater than the diameter of opening 118 and the diameter of portion 114b of cavity 114 to allow ball 120 to completely block opening 118 and portion 114b, as discussed herein.

Figure 15:
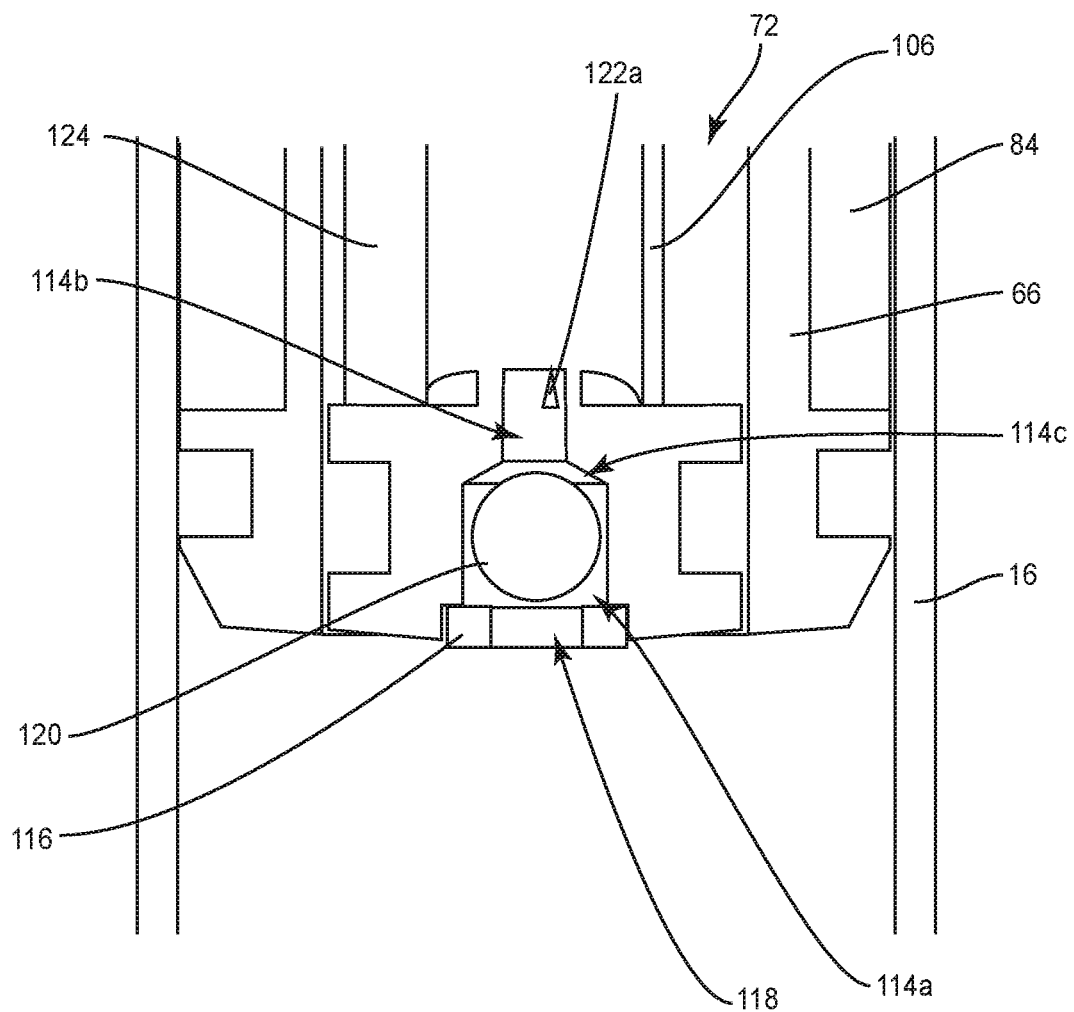
FIG. 15 is a side, cross sectional view of portions of components of the system shown in FIG. 1.
Figure 16:
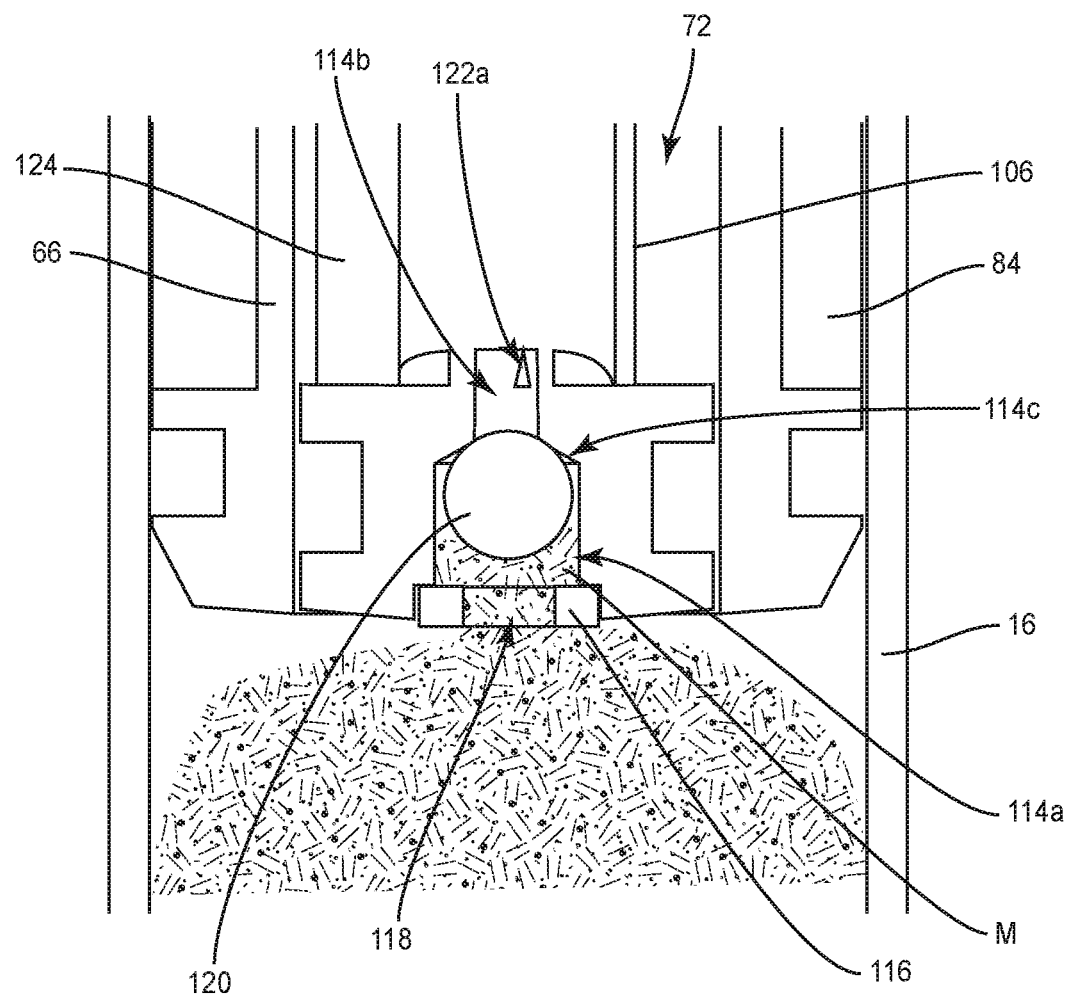
FIG. 16 is a side, cross sectional view of portions of components of the system shown in FIG. 1.

Valve 112 is movable between a first position, shown in FIG. 13 a second position, shown in FIG. 15, and a third position shown in FIG. 16. In particular, gravity will cause a portion of ball 120 to be positioned within opening 118 such that ball 120 completely blocks or closes opening 118, as shown in FIG. 13. When plunger 96 is moved axially relative to extension 16 and/or plunger 60 in the direction shown by arrow A in FIG. 2, air within passageway 32 of extension 16 and/or lumen 72 of plunger 60 will move ball 120 upwardly within cavity 114 toward portion 114b of cavity 114 such that ball 120 floats within portion 114a of cavity 114, as shown in FIG. 15, to allow the air to move around ball 120 and into portion 114b of cavity 114. The air then moves out of portion 114b through vent hole 122 such that the air exits plunger 96 through end 122b of vent hole 122. This allows the air to move into a portion of lumen 72 that is positioned above tip 104 such that the air can move into the environment surrounding system 10 through a proximal opening in lumen 72. When a material, such as, for example material M moves into portion 114a of cavity 114 through opening 118, material M moves ball 120 upwardly within cavity 114 toward portion 114b of cavity 114 such that ball 120 seats within tapered portion 114c of cavity 114 and blocks material M from moving into portion 114b of cavity 114, as shown in FIG. 16. In some embodiments, end surface 20 of base 14 includes a central protrusion 20a, as shown in FIGS. 9 and 10. Protrusion 20 is positioned within opening 118 when plunger 60 is fully inserted into extension 16 and plunger 96 is fully inserted into plunger 60.

In some embodiments, plunger 96 includes spaced apart struts 124 that each extend continuously from tip 104 to flange 102. Struts 124 are disposed radially about body 106. In some embodiments, struts 124 are evenly spaced apart from one another. Struts 124 each have a convexly curved outer surface. The outer surfaces of struts 124 are continuously curved along the length of struts 124 and conform to the curvature of surface 68 of plunger 60 such that the outer surfaces of struts 124 directly engage surface 68 and form an air tight and/or water tight seal with surface 68 as plunger 96 translates axially in opposite directions within lumen 72. Men the outer surfaces of struts 124 directly engage surface 68, body 106 of plunger 96 is spaced apart from surface 68, as shown in FIGS. 9 and 10, for example.

In operation and use, system 10 may be used to mix and/or dispense material M. In some embodiments, material M comprises a material, such as, for example, a liquid, gel, paste, cement, gum, ointment, cream and/or foam. In some embodiments, material M comprises a bone filler material, such as, for example, bone cement. In some embodiments, the bone cement comprises a poly(methyl methacrylate) (PMMA); methyl methacrylate (MMA); calcium phosphate; a resorbable polymer, such as, for example, PLA, PGA or combinations thereof; a resorbable polymer with allograft, such as, for example, particles or fibers of mineralized bone; Plexur® sold by Osteotech, Inc., or combinations thereof. In some embodiments, the bone cement is a high viscosity bone cement. In some embodiments, the bone cement has a viscosity that is at least 500 Pascal-sec (Pa-s) to infiltrate a medical site and prevent any migration of the bone cement during medical procedures. In some embodiments, the bone cement has a viscosity that is at least 600 Pa-s. In some embodiments, the bone cement has a viscosity that is at least 800 Pa-s. In some embodiments, the bone cement has a viscosity that is at least 1,000 Pa-s. In some embodiments, the bone cement comprises a liquid component and a powder component. In some embodiments, the liquid component and the powder component are mixed or otherwise combined such that the bone cement has a viscosity of at least 500 Pa-s at 2 minutes after the initiation of mixing the two components. In some embodiments, the liquid component and the powder component are mixed or otherwise combined such that the bone cement has a viscosity of at least 500 Pa-s at 5 minutes after the initiation of mixing the two components. In some embodiments, the liquid component and the powder component are mixed or otherwise combined such that the bone cement has a viscosity of at least 500 Pa-s after 10 minutes or more from the initiation of mixing the two components. In some embodiments, the bone cement comprises a polymerization accelerator.

Material M is inserted into passageway 32 such that material M is positioned at the bottom of passageway 32 and/or contacts end surface 20 of base 14. Material M is inserted into passageway 32 when valve 52 is in the first orientation discussed above and shown in FIGS. 1-3 and 12 such that valve 54 blocks channel 56. In some embodiments wherein material M comprises multiple components, such as, for example, a liquid component and a powder component, the components of material M may be mixed prior to inserting material M into passageway 32. The mixed material M may then be inserted into passageway 36, as discussed herein. In some embodiments wherein material M comprises multiple components, such as, for example, a liquid component and a powder component, the components of material M may be mixed within passageway 32, as discussed herein. In some embodiments, the components of may be mixed within passageway 32 or outside of passageway 32 using pressure, mechanical agitation, static mixing, or combinations thereof.

After material M is inserted into passageway 32, tip 104 and body 106 of plunger 96 are inserted into lumen 72 of plunger 60, as discussed herein, to form a plunger assembly. When plunger 96 is inserted into lumen 72 to form the plunger assembly, bottom surface 102a of flange 102 directly engages top surface 82c of flange 82, as discussed herein and shown in FIG. 2. When plunger 96 is inserted into lumen 72, the outer surface of tip 104 and/or an O-ring that is positioned within groove 110 directly engages surface 68 of plunger 60 to form an air tight or water tight seal with surface 68, as discussed herein. The plunger assembly is inserted into passageway 32 such that end surface 62 of plunger 60 is spaced apart from end surface 20 of base 14 that defines the bottom of passageway 32, as shown in FIG.

Figure 2:
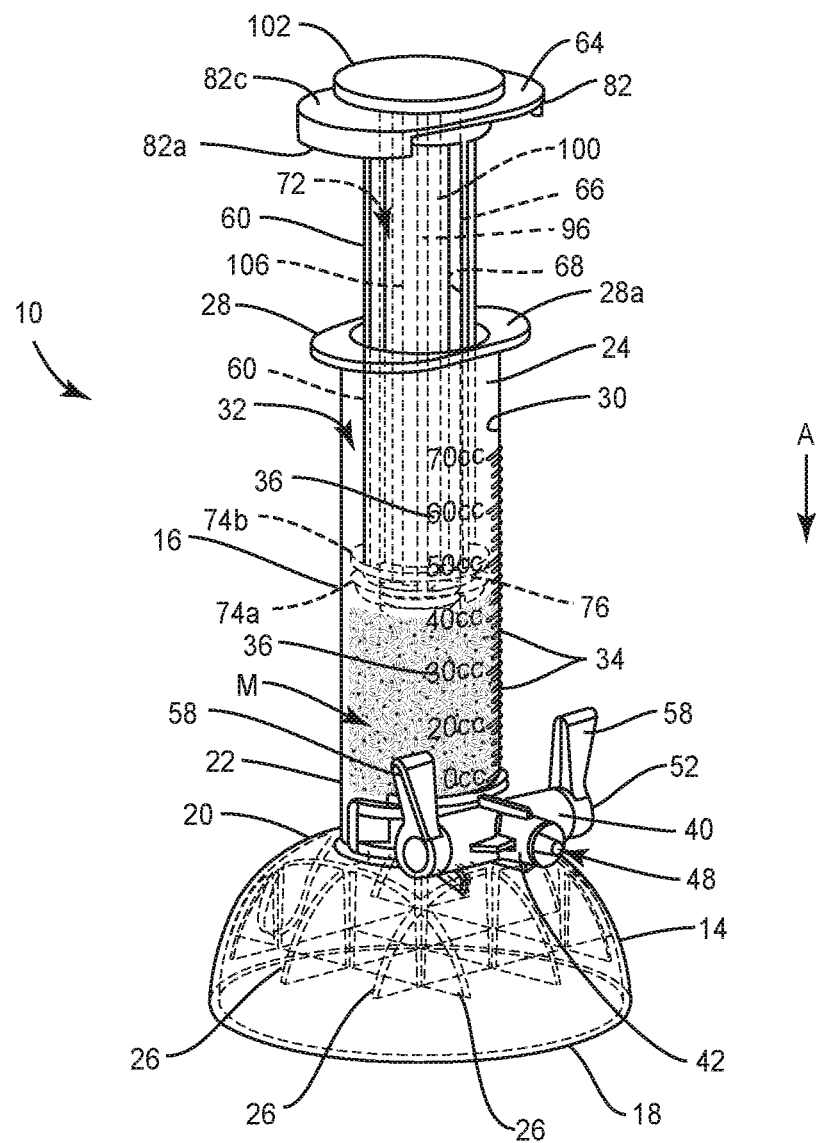
FIG. 2 is a side, perspective view, in part phantom, of components of the system shown in FIG. 1.

2. When the plunger assembly is inserted into passageway 32, outer surfaces of lips 74a, 74b and/or O-ring 76 of plunger 60 form an air tight and/or water tight seal with surface 30 of extension 16, as discussed herein. As the plunger assembly is inserted into passageway 32, air within passageway 32 can escape through valve 112 of plunger 96, as discussed herein. In some embodiments, the plunger assembly is inserted into passageway 32 such that end surface 62 of plunger 60 touches material M. In some embodiments, the plunger assembly is inserted into passageway 32 such that end surface 62 of plunger 60 is spaced apart from material M, as shown in FIG. 2. In some embodiments, the amount that the plunger assembly is inserted into passageway 32 depends upon the volume of material M within passageway 32. For example, the plunger assembly may be inserted farther into passageway 32 when the volume of material M within passageway 32 is less. However, when the volume of material M within passageway 32 increases, the plunger assembly is not inserted into passageway as far.

Figure 3:
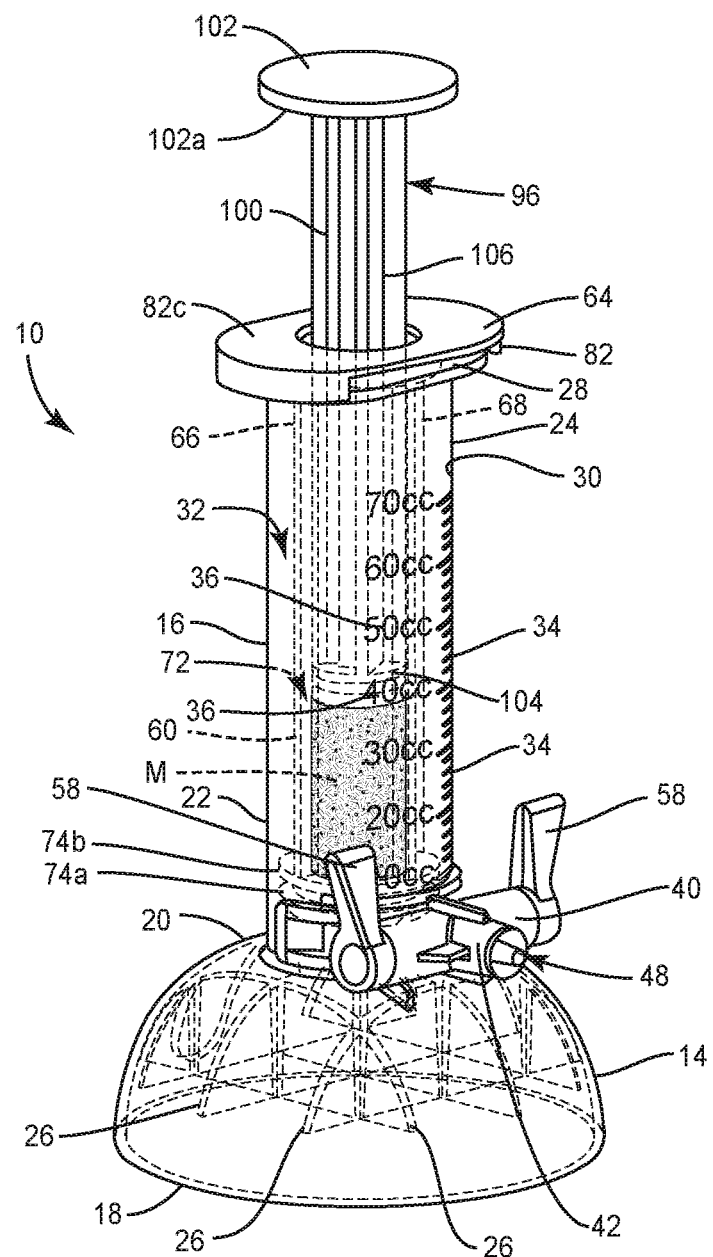
FIG. 3 is a side, perspective view, in part phantom, of components of the system shown in FIG. 1.

Plunger 60 is moved axially relative to main body 12 and plunger 96 within passageway 32 in the direction shown by arrow A in FIG. 2 such that end surface 62 of plunger 60 engages the wall that defines the bottom of passageway 32, as shown in FIG. 3. When end surface 62 of plunger 60 engages the wall that defines the bottom of passageway 32, plunger 60 is fully seated within passageway 32. In some embodiments, plunger 60 is connected with extension 16 by forming moving the twist lock discussed herein and shown in FIGS. 7-11 from the unlocked position to the locked position to fix plunger 60 relative to extension 16 such that plunger 60 is prevented from moving axially relative to extension 16. In some embodiments, plunger 60 is connected with extension 16 using cap 86, as discussed herein, to fix plunger 60 relative to extension 16 such that plunger 60 is prevented from moving axially relative to extension 16. As plunger 60 moves relative to main body 12 and plunger 96 in the direction shown by arrow A, material M moves into lumen 72 of plunger 60, as shown in FIGS. 3 and 4. Because lumen 72 has a smaller diameter than passageway 32, the same amount of input force creates more pressure on material M than would be created if lumen did not extend through end surface 62 of plunger. This amplification of pressure means that less effort is needed in dispensing material M. In some embodiments, plunger 60 is moved relative to main body 12 and plunger 96 in the direction shown by arrow A until bottom surface 82a of flange 82 of plunger 60 directly engages top surface 28a of flange 28 of extension 16, as discussed herein and shown in FIG. 3. As plunger 60 is moved relative to main body 12 and plunger 96 in the direction shown by arrow A, flange 102 of plunger 96 becomes spaced apart from flange 82 of plunger 60, as shown in FIGS. 3 and 4.

Figure 5:
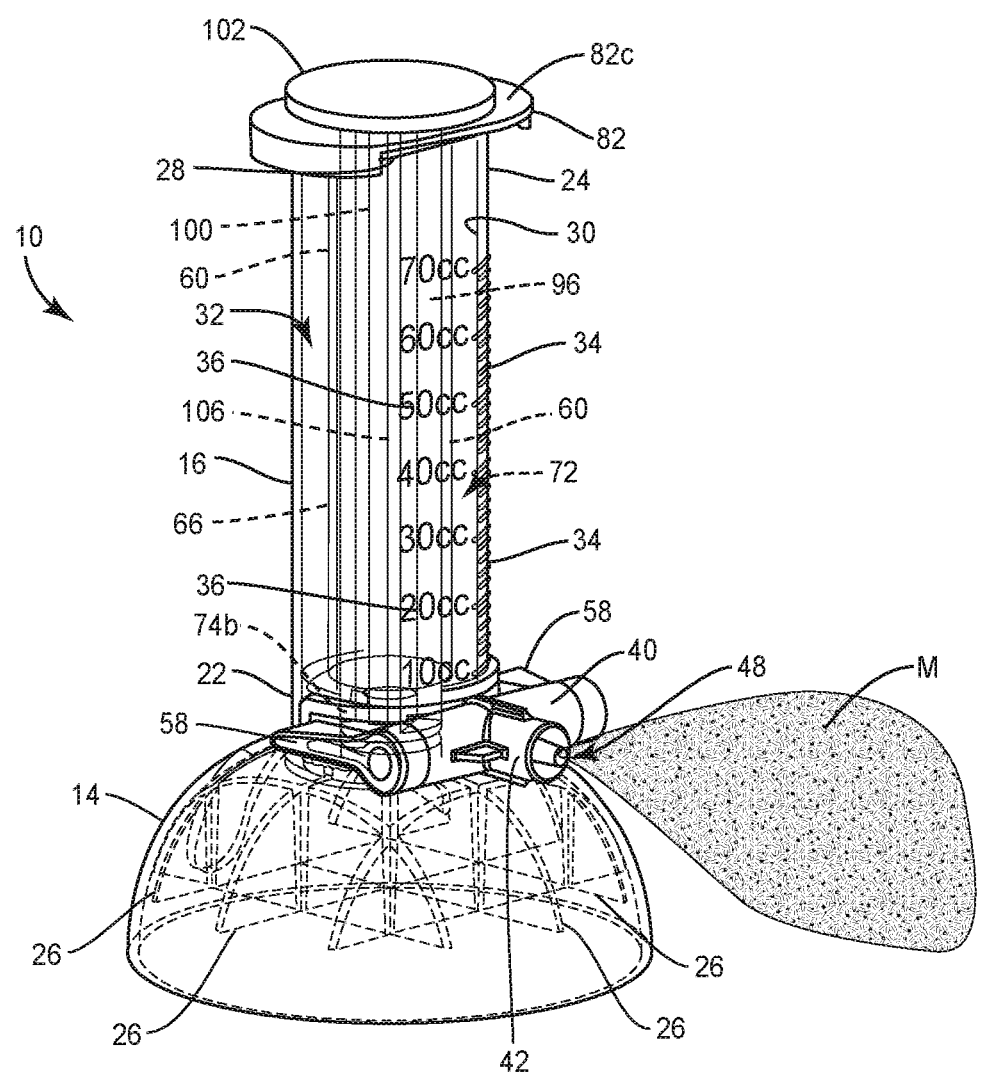
FIG. 5 is a side, perspective view, in part phantom, of components of the system shown in FIG. 1.
Figure 6:
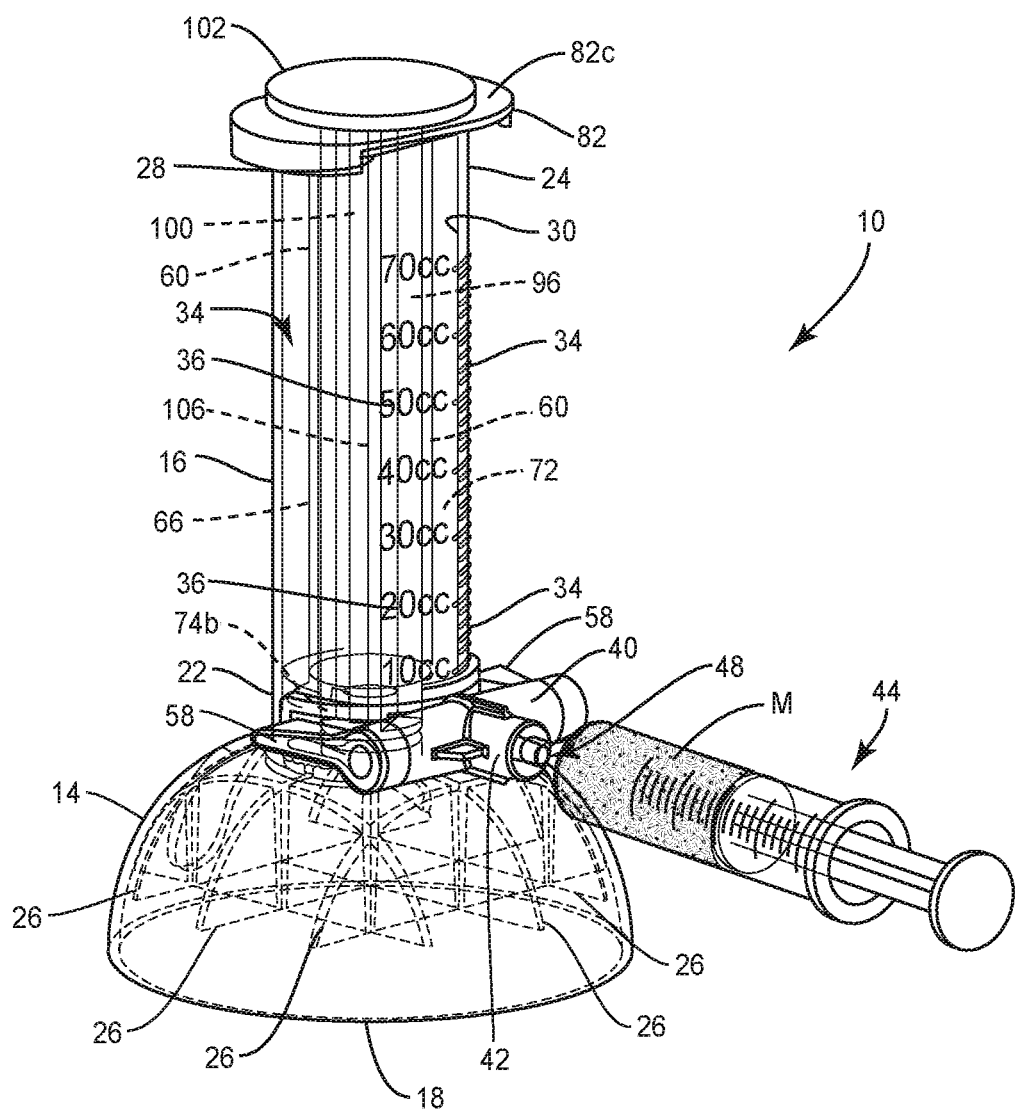
FIG. 6 is a side, perspective view, in part phantom, of components of the system shown in FIG. 1.

Valve 52 is moved from the first orientation, shown in FIGS. 1-3, 7, 8 and 12, in which valve body 54 blocks channel 56 to the second orientation, shown in FIGS. 4-6, by rotating valve body 54 relative to fitting 40 such that channel 56 is aligned with opening 38 and duct 48, as discussed herein and shown in FIG. 4. In some embodiments, cap 86 is coupled to extension 16 and plunger 60 such that surface 94 of part 88 engages surface of part 90 and flanges 28, 82 are disposed in cavities 95 of parts 88, 90 to fix plunger 60 relative to main body 12, as discussed herein. In some embodiments, part 88 remains removably coupled to part 90 after flanges 28, 82 are disposed in cavities 95. In some embodiments, part 88 may be permanently joined with part 90 by applying an adhesive to one or both of surfaces 94, for example.

After valve 52 is moved from the first orientation to the second orientation, plunger 96 is moved axially relative to main body 12 and plunger 20 in the direction shown by arrow A such that tip 104 of plunger 96 pushes material M out of lumen 72 and through opening 38, channel 56 and duct 48, as shown in FIG. 5. Plunger 96 may be moved axially relative to main body 12 and plunger 20 until bottom surface 102a of flange 102 directly engages a top surface 82c of flange 82, as also shown in FIG. 5, so as to push all of material M out of lumen 72 and through opening 38, channel 56 and duct 48. In some embodiments, syringe 44 may be coupled to hub 42 of fitting 40 prior to moving plunger 96 axially relative to main body 12 and plunger 60 such that material M moves out of lumen 72, through opening 48 and into syringe 44 when plunger 96 is moved axially relative to main body 12 and plunger 20, as shown in FIG. 6. A medical practitioner may then remove syringe 44 from hub 42 and inject material M from syringe 44 and into hole(s), fracture(s), void(s), depression(s), etc. in bone to fill the same, at least partly, with material M to maintain or improve the bone's structural integrity.

In some embodiments, system 10 may be used as a single stage plunger. In such embodiments, material M is inserted into passageway 32 such that material M is positioned at the bottom of passageway 32 and/or contacts end surface 20 of base 14. The plunger assembly is then inserted into passageway 32. As the plunger assembly is inserted into passageway 32, air within passageway 32 of extension can exit passageway 32 through valve 112 of plunger 96, as discussed herein. The plunger assembly then pushes material M through opening 38, channel 56 and duct 48. In some embodiments, syringe 44 may be coupled to hub 42 of fitting 40 prior to moving the plunger assembly relative to main body 12 such that material M moves through opening 48 and into syringe 44 when the plunger assembly is moved axially relative to main body 12 and plunger 20 A medical practitioner may then remove syringe 44 from hub 42 and inject material M from syringe 44 and into hole(s), fracture(s), void(s), depression(s), etc. in bone to fill the same, at least partly, with material M to maintain or improve the bone's structural integrity.

In some embodiments, a kit containing one or more components of dispensing system 10 is provided. The kit may include components from any of the embodiments discussed herein. In some embodiments, material M is bone cement, as discussed herein, and the kit includes instructions for mixing and/or dispensing the bone cement using the contents of the kit.

Example 1

A two-stage mixer plunger, similar to the device of system 10 discussed herein was tested to determine the difference in force required to plunge the plunger for plunging bone cement. The test was conducted at 18° C. The two-stage mixer plunger includes a bayonet mount two stage plunger that clips onto a mixer of the two-stage mixer plunger. The two-stage mixer plunger used in this test is the same as the embodiments discussed herein that do not include cap 86, such as, for example, the embodiments wherein flanges 28, 82 form a twist lock, as discussed herein. The two-stage mixer plunger performed as follows:

Two-Stage Mixer Plunger (Bayonet)

| Time | Force (lb) | Volume dispensed (running total) |
|---|---|---|
| 2:00 | 18 | 1 |
| 2:30 | 13 | 2 |
| 3:00 | 17 | 3 |
| 3:30 | 20 | 4 |
| 4:00 | 21 | 5 |
| 4:30 | 28 | 6 |
| 5:00 | 40 | N/A |

Example 2

A two-stage mixer plunger, similar to the device of system 10 discussed herein was tested to determine the difference in force required to plunge the plunger for plunging bone cement. The test was conducted at 18° C. The two-stage mixer plunger includes separate clips to hold the first stage plunger onto the mixer. The two-stage mixer plunger used in this test is the same as the embodiments discussed herein and shown in FIG. 7 that include cap 86. The two-stage mixer plunger performed as follows:

Two-Stage Mixer Plunger (Clips)

| Time | Force (lb) | Volume dispensed (running total) |
|---|---|---|
| 2:00 | 21 | 1.5 |
| 2:30 | 11 | 2.25 |
| 3:00 | 16 | 3 |
| 3:30 | 21 | 4 |
| 4:00 | 26 | 5 |
| 4:30 | 38 | 6 |
| 5:00 | 41 | 7 |
| 5:30 | 52 | 8 |

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A dispensing system comprising:
a main body comprising a base and an extension extending from the base, the extension defining a longitudinal axis, the extension comprising an inner surface defining a passageway, the main body comprising an opening that extends transverse to the longitudinal axis, the opening being in communication with the passageway;
a first plunger including a first plunger body positioned within the passageway, the first plunger body comprising a lumen extending through and between opposite proximal and distal end surfaces of the first plunger; and
a second plunger including a second plunger body positioned within the lumen, the second plunger body comprising opposite proximal and distal ends, the distal end being configured to move a material positioned in the lumen out of the opening, the distal end comprising a vent valve configured to allow air within the lumen to exit the second plunger body through the vent valve when the second plunger body is inserted into the lumen, the vent valve including a cavity and an aperture that extends through a distal end surface of the distal end of the second plunger body, the aperture being in communication with the cavity, the cavity extending through a proximal end surface of the proximal end.

2. A dispensing system as recited in claim 1, wherein the extension comprises a fitting, the opening extending through the fitting, the dispensing system comprising a syringe that is configured to be coupled to the fitting such that the material moves out of the opening and into the syringe.

3. A dispensing system as recited in claim 2, wherein the dispensing system comprises a second valve that is coupled to the fitting, the second valve comprising a channel, the second valve being movable between a first orientation in which the channel is offset from the opening and a second orientation in which the channel is aligned with the opening.

4. A dispensing system as recited in claim 1, wherein a proximal end of the first plunger body comprises a flange that engages a flange of the extension when the first plunger body is fully inserted into the passageway.

5. A dispensing system as recited in claim 4, further comprising a cap removably coupled to the first plunger and the extension, the cap including a cavity configured for disposal of the flanges to fix the first plunger relative to the main body, the cap including a first part and a second part that is separable from the first part.

6. A dispensing system as recited in claim 4, wherein the flange of the first plunger body engages a flange of the second plunger body when the second plunger body is fully inserted into the lumen.

7. A dispensing system as recited in claim 1, wherein a distal end of the first plunger body comprises an enlarged portion that forms a seal with the inner surface.

8. A dispensing system as recited in claim 1, wherein an outer surface of the second plunger body forms a seal with an inner surface of the first plunger body that defines the lumen.

9. A dispensing system as recited in claim 1, wherein the first plunger body includes an outer surface and an opposite inner surface that defines the lumen, the first plunger comprising spaced apart struts that each extend outwardly from the first plunger body, outer surfaces of the struts directly engaging the inner surface of the extension to form an air tight seal with the inner surface of the extension when the first plunger body is positioned within the passageway.

10. A dispensing system as recited in claim 1, wherein the second plunger body includes an outer surface and an opposite inner surface, the second plunger comprising spaced apart struts that each extend outwardly from the second plunger body, outer surfaces of the struts directly a surface of the first plunger body that defines the lumen to form an air tight seal with the first plunger when the second plunger body is positioned within the lumen.

11. A dispensing system as recited in claim 1, wherein the vent valve includes a ball positioned within the cavity.

12. A method of dispensing a material, the method comprising:
positioning a material in a passageway of a main body, the main body comprising a base and an extension extending from the base, the extension defining a longitudinal axis, the extension comprising an inner surface defining the passageway, the main body comprising an opening that extends perpendicular to the longitudinal axis, the opening being in communication with the passageway;
inserting a plunger body of a second plunger into a lumen of a first plunger, the plunger body comprising opposite proximal and distal ends, the distal end comprising a vent valve configured to allow air within the lumen to exit the plunger body through the vent valve when the plunger body is inserted into the lumen, the vent valve including a cavity and an aperture that extends through a distal end surface of the distal end of the plunger body, the aperture being in communication with the cavity, the cavity extending through a proximal end surface of the proximal end;

inserting the first plunger into the passageway such that the material moves into the lumen; and translating the second plunger axially within the lumen such that the material moves through the opening.

13. A method as recited in claim 12, wherein the extension comprises a proximal end and an opposite distal end, the distal end of the extension defining a bottommost portion of the passageway, the distal end of the extension being coupled to the base, a fitting being coupled to the extension between the proximal and distal ends of the extension, the opening extending through the fitting, the main body comprising a second valve that is coupled to the fitting, the valve comprising a channel, the method further comprising moving the valve from a first orientation in which the channel is offset from the opening to a second orientation in which the channel is aligned with the opening.

14. A method as recited in claim 13, wherein the material is prevented from moving through the opening when the valve is in the first orientation and the material is able to move through the opening when the valve is in the second orientation.

15. A method as recited in claim 12, further comprising coupling a syringe to the opening and drawing the material into the syringe.

16. A method as recited in claim 12, wherein inserting the first plunger into the passageway comprises translating the first plunger within the extension until a flange of the first plunger engages a flange of the extension.

17. A method as recited in claim 16, wherein translating the second plunger axially within the lumen comprises translating the second plunger axially within the lumen until a flange of the proximal end of the plunger body engages the flange of the first plunger.

18. A dispensing system comprising:
- a monolithic main body comprising a base and an extension extending from the base, the extension defining a longitudinal axis, the extension comprising an inner surface defining a passageway, the main body comprising an opening that extends perpendicular to the longitudinal axis, the opening being in communication with the passageway;
- a fitting coupled to the extension, the opening extending through the fitting;
- a valve coupled to the fitting, the valve comprising a channel, the valve being movable between a first orientation in which the channel is offset from the opening and a second orientation in which the channel is aligned with the opening;
- a first plunger including a first plunger body movably positioned within the passageway, the first plunger body comprising a lumen extending through and between opposite proximal and distal end surfaces of the first plunger body, a distal end of the first plunger body comprising an enlarged portion that forms a seal with the inner surface;
- a second plunger including a second plunger body movably positioned within the lumen, an outer surface of the second plunger forming a seal with an inner surface of the first plunger that defines the lumen, the second plunger body comprising opposite proximal and distal ends, the distal end comprising a vent valve configured to allow air within the lumen to exit the second plunger body through the vent valve when the second plunger body is inserted into the lumen, the vent valve including a cavity and an aperture that extends through a distal end surface of the distal end of the second plunger body, the aperture being in communication with the cavity, the cavity extending through a proximal end surface of the proximal end of the second plunger body, a spherical ball being positioned within the cavity;
- bone cement positioned within the lumen; and
- a syringe coupled to the fitting,
- wherein a proximal end of the first plunger body comprises a flange that engages a flange of the extension when the first plunger body is fully inserted into the passageway, the flange of the first plunger body engaging a flange of the second plunger body when the second plunger body is fully inserted into the lumen, and
- wherein the vent valve is movable between a first configuration in which the ball blocks the aperture and air within the lumen is prevented from exiting the second plunger body through the vent valve and a second configuration in which the ball does not block the aperture and air within the lumen is able to exit the second plunger body through the vent valve.

19. A dispensing system as recited in claim 1, wherein the extension is integrally formed with the base.

20. A dispensing system as recited in claim 1, wherein the cavity comprises a first portion and a second portion, a ball being positioned within the first portion, the second portion extending through the proximal end surface, the ball having a diameter that is greater than a diameter of the second portion and a diameter of the aperture.

* * * * *